(12) United States Patent
Hodgen

(10) Patent No.: US 6,258,802 B1
(45) Date of Patent: Jul. 10, 2001

(54) CORTICOID THERAPY

(75) Inventor: Gary D. Hodgen, Virginia Beach, VA (US)

(73) Assignee: Medical College of Hampton Roads, Norfolk, VA (US)

(*) Notice: Subject to any disclaimer, the term of this patent is extended or adjusted under 35 U.S.C. 154(b) by 0 days.

(21) Appl. No.: 09/413,421

(22) Filed: Oct. 6, 1999

(51) Int. Cl.7 .................. A61K 31/56; A61K 31/445; A61K 31/135
(52) U.S. Cl. ............... 514/169; 514/171; 514/324; 514/651
(58) Field of Search ..................... 514/169, 171, 514/324, 651

(56) References Cited

PUBLICATIONS

Drug Facts and Comparisons; 1996 edition, Nov. 1995.*
Physicians' Desk Reference; 53 Edition 1999, Dec. 1998.*
Beall et al.; "Clomiphene protects against Osteoporosis in the mature ovariectomized rat"; Calcif. Tissue Int. (1984), 36(1), 123–5; ISSN: 0171–967x.*

* cited by examiner

Primary Examiner—Theodore J. Criares
Assistant Examiner—Jennifer Kim
(74) Attorney, Agent, or Firm—Ostrolenk, Faber, Gerb & Soffen, LLP

(57) ABSTRACT

Treatments in which a progestational corticoid active compound is administered are improved by additionally administering a selective estrogen receptor modulator.

20 Claims, No Drawings

CORTICOID THERAPY

BACKGROUND OF THE INVENTION

The use of corticoids for a variety of indications is well known. They are used to treat, for example, asthma, rheumatoid arthritis and auto-immune diseases, including lupus, Scleroderma, Wegener's granulomatiosis, and the like. Some corticoids also exhibit progestational activity. One example is triamcinolone acetonide. The usefulness of such progestational corticoids is often impaired in some women by the side effects of such agents. For instance, those major side effect include menstrual irregularity and/or hot flashes. Such side effects can result in reluctance or even avoidance of the use of the corticoid as well as to restrict the medicinal formulations, such as inhalation therapies versus oral tablets or other systemic delivery systems or routes. Among females and males, reproductive capabilities can be impaired when corticoidal therapies are administered.

It has now been discovered that the side effects of the progestational corticoids can be modulated by the cojoint use of a selective estrogen receptor modulator (also known as an SERM, selective estrogen or anti-estrogen).

The use of an anti-estrogen in medical practice is known. While the anti-estrogen therapy which has been developed has been successful, it is not without problems. One reason is that endogenous hormone production implicates a hyperactivity of the hypothalamic-pituitary-gonadal axis. When estrogen binds to its receptors, there is a feedback mechanism which becomes activated and regulates the endogenous production of pituitary gonadotropins and, in turn, estrogen, so that the hormonal milieu remains within the physiological range. However, when an anti-estrogen binds to the estrogen receptors, altered estrogen feedback mechanisms are implicated in a pharmacological manner compared to what occurs when estrogen binds normally. The anti-estrogens themselves can induce multiple follicular growth which, in turn, causes the production of endogenous ovarian estrogens. One example is the use of clomiphene or tamoxifen for ovulation induction. At the time of the first anti-estrogen dose administration and continuing for some period of time, the endogenous estrogen produced as a consequence of the multiple follicular growth may not appear to pose a problem. However, at some point, which is totally unpredictable and which varies from individual to individual, endogenous estrogen can be produced such that the quantity of estrogen present can elevate blood levels well above 300 pg/ml. Indeed, estradiol concentration in plasma may exceed a few thousand pg/ml in some instances. Therefore, while the use of an anti-estrogen seeks to reduce or modify or eliminate the side effects of estrogen, its use over time may have the reverse effect by inducing an excess concentration of estrogen. Not only may the use of the anti-estrogen exaggerate the estrogen side effects which the therapeutic course seeks to avoid, but the anti-estrogen may also even eliminate the primary benefit of its administration in the first instance. For example, a "run away" endogenous estrogen can induce ovulation in those situations where the administration of the anti-estrogen was designed to provide contraception. This feature of anti-estrogen therapy makes the establishment and maintenance of appropriate dosages of anti-estrogen difficult and in some cases impossible, especially when the therapeutic goal is simultaneously to limit excessive estrogenic impact in one tissue while providing adequate estrogenic stimulation in another tissue.

In light of the characteristics of the anti-estrogen, the discovery that it can be used to modify the side effects of corticoid therapy is surprising and unexpected. By this combination, patients can better tolerate higher corticoid doses, with fewer side effects, as well as a broader array of drug delivery systems.

It is the object of this invention to modify the side effects of the use of progestational corticoids. This and other objects of the invention will become apparent to those of ordinary skill in the art from the following detailed description.

SUMMARY OF THE INVENTION

This invention relates to a method of using a glucocorticoid and modifying the side effects thereof by use of a SERM such as tamoxifen. More particularly, the invention involves superposing the use of a selective estrogen receptor modulator on the administration of a glucocorticoid compound which also exhibits substantial progestin-like activity in an overlapping dose range.

DETAILED DESCRIPTION OF THE INVENTION

Corticoids which exhibit progestin-like activity are employed in the present invention to treat a variety of indications in accordance with their well known activity. They can thus be used to treat, for example, asthma, rheumatoid arthritis and a variety of auto-immune diseases, including lupus, scleroderma, Wegener's granulomatosis, and the like. Examples of such progestational corticoid compounds which can be utilized include triamcinolone acetonide, fluticasone propionate, mometasone furoate, beclomethoasone dipropionate, budesonide, prednisone, and the like. Other examples of such progestational corticoid active compounds arc well known in the art.

The formulation of dosage forms containing the corticoid, as well as the dosage amount and mode of administration are those known in the art. The progestational corticoid active compound can thus be administered by way of any art recognized means as practiced in the pharmaceutical arts. For example, it can be formulated so that it is administered orally, subcutaneously, intramuscularly, buccally, by inhalation, by a skin patch for transdermal absorption, contained within an inert matrix which is implanted within the body and in the depot state or intravaginally in a matrix that releases the material.

In accordance with the present invention, an additional therapy, namely the use of a selective estrogen reception modulator (also known as an SERM, selective estrogen or anti-estrogen) is superposed on the known use of the corticoid.

Any known SERM can be used in the practice of this invention. Examples of known SERMs include, but are not limited to, clomiphene; cycladiene; tamoxifen; nafoxidine; nitromifene citrate (N-55,945-27); 13-ethyl-17α-ethynl-17β-hydroxygona-4-9-11-trien-3-one (R2323); diphenol hydrochryscne; erythro-MEA; allenolic acid; cyclofenyl; chlorotrianisene; ethamoxytriphetol; triparanol; CI-626; CI-680; MER-25; U-11,555A; U-11,100A; ICI-46,669; ICI-46,474; CN-55,945; compounds of the formula:

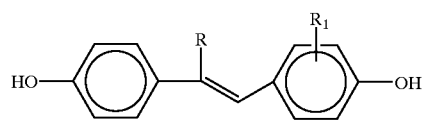

where $R_1$ is hydrogen, an aromatic group or alkyl of preferably no more than nine carbon atoms, R is an aromatic or alkyl group of preferably no more than nine carbon atoms and various of their derivatives; the triphenyl compounds described in U.S. Pat. No. 2,914,563 which are of the formula:

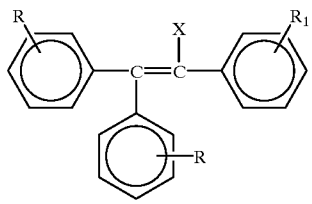

wherein one of the R groups is a basic ether of the formula $OC_nH_{2n}A$ in which n is 2, 3 or 4 and A is a $C_{1-4}$ dialkylamino group, N-piperidyl or β-morpholinyl and the other R and $R_1$ are hydrogen, halogen or methoxy while X is halogen; as well as benzothiophenes such as those described in U.S. Pat. No. 5,624,940 of the formula:

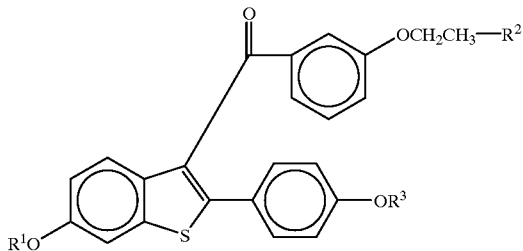

in which R and $R^3$ are independently hydrogen, $C_{1-4}$ alkyl, —CO($C_{1-6}$alkyl) or —COAr in which Ar is optionally substituted phenyl, $R^2$ is pyrrolidino, hexamethyleneamino or piperidino, or a salt thereof. Example of the benzothiophenes include raloxifene (6-hydroxy-2-(4-hydroxyphenyl)-3-[4-(2-piperidinethoxy)-benzoyl] benzo[b]- thiophene) and LY353381.HCl benzothyphenes. The SERMs can also be employed in the form of their pharmaceutical acceptable non-toxic salt or complexes. Examples include the acid addition salt such as, for instance, citrate, hydrochloride, hydrobromide, sulfate, phosphate, nitrate, oxalate, fumarate, gluconate, tannate, maleate, acetate, benzoate, succinate, alginate, maleate, absorbate, tartrate and the like. The complexes can be with metals or various organic moietics.

The SERM aspect of the present invention is similar to the previous use of such materials for the treatment of estrogen dependent or other medical conditions. Thus, not only may any known SERM or anti-estrogen be employed, but also the dosage amount and mode of administration heretofore employed can also be employed in the practice of the present invention. Those SERMs which have an asymmetric atom can be used as the racemate or in any of the chiral or entomeric forms or mixture of such forms. For example, clomiphene can be used with an array of isomeric ratios (EN:ZU), as well as employing only one of the isomers. Thus, the route of administration can be in any conventional route where the SERM is active, for instance orally, by inhalation, intravenously, subcutaneously, intramuscularly, sublingually, percutaneously, rectally, intranasally or intravaginally. Similarly, the administration form can be a tablet, dragee, capsule, pill, nasal mist, aerosol, pellet, implant (or other depot) and the like.

Some SERMs have been indicated for the prevention of post-menopausal osteoporosis, modulation of serum lipid profiles and breast cancer prevention. To the extent such activity is also realized when the SERM is used in accordance with the present invention, it augments the usefulness of the combination (SERM with corticoid).

The amount of the SERM which is administered can be that which is effective to regulate endogenous estrogen secretions to a desired level. Thereby, ovulation can be blocked and endometrial growth and menstruation can be controlled, as desired. As a general proposition, the dosage is sufficient to establish a blood estrogen (endogenous) concentration achieved in the range of about 10 to 125 pg/ml and more preferable about 40 to 90 pg/ml, although other values can be selected if desired.

Formulations containing the SERM or the progestational corticoid active compound, together with a suitable carrier, can be a solid dosage form which includes tablets, capsules, cachets, pellets, pills, powders and granules; topical dosage forms which include solutions, powders, fluid emulsions, fluid suspensions, semi-solids, ointments, pastes, creams, gels or jellies and foams; and parential dosages forms which include solutions, suspensions, emulsions or dry powder. The composition can in addition contain a pharmaceutical acceptable diluents, fillers, disintegrates, binders, lubricants, surfactants, hydrophobic vehicles, water soluble vehicles, emulsifiers, buffers, humeticants, moisturizers, solubilizers, preservatives and other means of augmenting the medicinal entity. The means and methods of administration are known in the art and the artisan can refer to various pharmalogic references for guidance. One such reference is "Modem Pharmaceuticals", Banker & Rhodes, Marcel Dekker, Inc. 1979 and another is Goodman & Gilman's, "The Pharmaceutical basis of therapeutics", 6th Ed., MacMillan Publishing Co., New York, 1980.

If desired, the two components, namely the SERM and the progestational corticoid active compound, can be coadministered utilizing the same or different dosage forms or means, for example, the same tablet. Application of the components, compositions and the methods of this invention for the medical and/or pharmaceutical use which are described in this text can thus be accomplished by any clinical, medical or pharmaceutical methods or techniques as are presently or prospectively known to those skilled in the art.

The administration of the components can be either periodic such as a weekly or monthly basis or continuous, that is on a daily administration. Daily administration is preferred because individuals are more likely to follow the treatment regimen and not to forget or overlook a periodic administration schedule. Amounts can be lowered or raised based on the administration regimen and based on the characteristics of the individual receiving the treatment. Variations of dosage based or the route of administration may vary and such changes can be determined practicing known techniques The pharmaceutical formulations can be provided in kit form containing a plurality of dosage units intended for ingestion on successive days. Preferably, the plurality is in multiples of seven.

In one preferred embodiment of the invention, the progestational corticoid active compound is administered in an amount sufficient to block ovarian follicular stimulation and ovulation. For example, primate data have shown that it takes less than 30 μg/day of triamcinolone acetonide to block ovulation. The dose required orally is different. By superposing a SERM such as, for example, tamoxifen, on this administration, it is possible to also achieve amenorrhea, with endometrial control.

In another preferred embodiment of the invention, the progestational corticoid active compound is employed for its usual corticoid activity in the treatment of asthma, lupus, etc, administered in an amount sufficient to achieve such activity while simultaneously preventing SERM-induced ovarian hyperstimulation and endometrial carcinoma via the co-presence of progestational activity. These SERM plus progestational corticoid combinations do not negate the SERMS capacities to prevent breast cancer. The SERM is administered to realize high rates of amenorrhea, control hot flashes, reduce the risk of breast cancer, prevent osteoporosis and cardiovascular disease, etc.

In order to further illustrate the present invention, specific examples are set forth below. It would be appreciated, however, that these examples are illustrative only and are not intended to limit the scope of the invention.

EXAMPLE

1. Clomiphene is used alone at 100 mg/day for the treatment of endometriosis. After 15 days, the serum estrogen reached 500 pg/ml. Triamcinolone acetonide at 75 mcg/day is then also administered.

2. Raloxifene at 60 mg/day and budesonide acetate at 12 mg/day were administrated to treat leiomyoma.

3. Example 1 is repeated using clomiphene EN:ZU isomers in a ratio of 8:1.

4. Clomiphene ZU isomer at 50 mg/day and prednisone at 12 mcg/day are coadministered.

5. Clomiphene is used alone at 100 mg/day for the treatment of endometriosis. After 15 days, the serum estrogen reached 500 pg/ml. Mometasone furoate at 100 to 800 mg/day is then also administered.

6. Example 5 is repeated using fluticasone propionate at a dosage of 2 to 10 mg/day in place of the mometasone furoate.

What is claimed is:

1. In a method of treating a condition in a host treatable by administration of a corticoid thereto by administering an effective amount of a corticoid to the host so as to manifest the corticoid activity in that host, the improvement which comprises employing progestational corticoid as said corticoid and additionally administering an effective amount of a selective estrogen receptor modulator to the host effective to modulate the bleeding side effect of said corticoid administration.

2. The method of claim 1 wherein the selective estrogen receptor modulatoi is clomiphene or tamoxifen or toremifene.

3. The method of claim 1 wherein the selective estrogen receptor modulator is a benzothiophene.

4. The method of claim 1 wherein the progestional corticoid is triamcinolone acetonide.

5. The method of claim 4 wherein the selective estrogen receptor modulator is clomiphene or tamoxifen.

6. The method of claim 4 wherein the selective estrogen receptor modulator is a benzothiophene.

7. The method of claim 1 wherein the host is a woman.

8. The method of claim 1 wherein the host is a pre-menopausal woman.

9. The method of claim 1 wherein the host is a post-menopausal woman.

10. The method of claim 7 wherein the amount of progestional corticoid is effective to treat asthma.

11. The method of claim 7 wherein the amount of progestational corticoid is effective to treat rheumatoid arthritis.

12. The method of claim 7 wherein the amount of progestational corticoid is effective to treat an auto-immune disease.

13. The method of claim 7 wherein the amount of progestational corticoid is effective to treat sclerodema.

14. The method of claim 7 wherein the amount of progestational corticoid is effective to treat a skin allergy.

15. A kit comprising a plurality of tablets containing an effective amount of a selective estrogen receptor modulator and an amount of a progestational corticoid effective to modulate the bleeding side effect of said corticoid administration.

16. The kit of claim 15 wherein the selective estrogen receptor modulator is clomiphene or tamoxifen.

17. The kit of claim 16 wherein the agent is triamcinolone acetonide.

18. The kit of claim 16 herein the selective estrogen receptor modulator is a benzothiophene.

19. The kit of claim 18 wherein the agent is triamcinolone acetonide.

20. The kit of claim 15 wherein said plurality is a multiple of seven.

* * * * *